United States Patent
Raissen

Patent Number: 5,900,251
Date of Patent: May 4, 1999

[54] INTERNAL BREATH FRESHENER AND DIGESTIVE AID

[75] Inventor: Anthony Raissen, Calabasas, Calif.

[73] Assignee: Breath Asure, Inc., Calabasas, Calif.

[21] Appl. No.: 08/869,693

[22] Filed: Jun. 5, 1997

Related U.S. Application Data

[60] Provisional application No. 60/019,541, Jun. 10, 1996.
[51] Int. Cl.⁶ ............................. A61K 9/48; A61K 35/78; A61K 47/44
[52] U.S. Cl. ....................... 424/456; 424/400; 424/195.1; 514/962; 514/783
[58] Field of Search ..................................... 424/400, 456, 424/195.1; 514/962, 783

[56] References Cited

U.S. PATENT DOCUMENTS 5,578,307 11/1996 Wunderlich et al. .

*Primary Examiner*—Edward J. Webman
*Attorney, Agent, or Firm*—John L. Chiatalas; Michael J. Brown; Trademark & Patent Counselors of America, P.C.

[57] ABSTRACT

An essentially herbal or herbal extract composition for the treatment and control of breath odors and aiding digestion, and method of treatment or control of breath odors and aiding digestion therewith. The preferred composition contains ginger, licorice, chamomile, parsley seed oil, and sunflower seed oil in a delivery system which is intended to be ingested and swallowed whole for delivery of the ingredients to the stomach and/or lower in the digestive tract.

8 Claims, No Drawings

INTERNAL BREATH FRESHENER AND DIGESTIVE AID

This application claims benefit of provisional application Ser. No. 60/019,541 filed Jun. 10, 1996.

FIELD OF THE INVENTION

The present invention relates to the field of breath fresheners, especially those that freshen breath by action in the stomach or by systemic effects on digestive processes, generally by aiding the digestive process. The invention further relates to the use of herbs and herbal extracts and/or oils in breath odor control. In addition, the invention relates to the use of herbs and/or herbal extracts to aid digestion.

BACKGROUND OF THE INVENTION

Problems with so called "bad breath" have plagued many animals, including humans as far as time can recall. Many different products and methods have been utilized to cover up these offensive odors at various points in time. Frequently, aromatic substances were used for local application to the oral cavity as a means to mask these offensive odors. These efforts have given rise to the enormous breath spray and breath lozenge industry. These products typically only mask the odors, and then for only a short time. They generally only act on the local environment of the oral cavity and upper end of the throat.

As more sophistication developed in this field, it was recognized that some of the offensive odors associated with breath were due to bacteria in the oral cavity, or decaying food particles retained in the mouth. An increased emphasis on brushing the teeth, gums, and tongue as well as greater emphasis on flossing, began to address some of the issues that mere breath mints, breath sprays, and mouthwashes and rinses could not address Unfortunately, these methods addressed only the local oral cavity and not any of the issues of more remote sources of the offensive odors.

Still more recently it has been recognized that much of the offense breath odors are actually not generated locally in the mouth and throat, but more remotely in the stomach and other portions of the intestinal tract. This is particularly evident with the breath from someone with heartburn and belching, where the breath may be heavily tainted with the smell of chyme, a particularly offensive odor. Other sources of offensive breath odor have been recognized as the elimination of substances directly through the lungs.

Digestive aids have been known for some time. Many of these are simply antacids, such as alkaline hydroxides or antacid/gas producing products, such as mineral carbonates and bicarbonates. Other digestive aids have been known in the herbal area, such as ginger, licorice, and chamomile. These substances have been known as flavorings (ginger and licorice); as carminatives (ginger and chamomile), as a remedy for indigestion generally (chamomile), as intestinal stimulants and/or laxatives (ginger and licorice) and as emetics (chamomile); These herbal properties show that the herbs are working in many differing areas to ease "gastrointestinal discomfort", which discomfort may be caused by excessive gas production, a slowing and distension of the upper or lower bowel, or retention in the stomach of an irritant or other noxious substance needing removal. (See particularly Remington: The Science and Practice of Pharmacy, 19th Edition, Mack Publishing, Easton, Pa. 1995, pp. 1387, 1391, 1393, & 1394; Pharmacognosy, 6th edition, Claus et al Editors, Lea & Febiger, Philadelphia, 1970, p 11, 112, & 214; and Martindale: the Extra Pharmacopoeia, 27th Edition, The Pharmaceutical Press, London, England, 1977). Carminative properties, which help to expel gases from the gastrointestinal tract, either through release via the oral and nasal cavities or through the lower intestine and rectum would also be expected to promote release of offensive odors originating in the stomach via one's breath This is clearly opposite the present invention's goal of improving or controlling offensive breath odors while simultaneously aiding digestion.

OBJECT OF THE INVENTION

It is therefore an object of the invention to provide a breath freshener product which acts at these more remote sites of the body.

It is another object of the invention to provide a breath freshener product which results in sustained control of offensive breath odor.

It is still another object of the invention to provide a method of controlling offensive breath odor elimination from the body.

Yet another object of the invention is to provide a product which aids digestion.

Still another object of the invention is to provide a product which helps to reduce or control offensive breath odors and simultaneously aid digestion.

An even further object of the invention is to provide a product which promotes offensive breath odor control through the dual action of breath freshening agents and digestive aids.

Other objects of the invention will be apparent to those of ordinary skill in the art.

SUMMARY OF THE INVENTION

These and other objects of the invention can be achieved by an essentially herbal or herbal extract composition for the treatment and control of breath odors and method of treatment or control of breath odors therewith. The preferred composition contains ginger, licorice, chamomile, parsley seed oil, and sunflower seed oil in a delivery system which is intended to be ingested and swallowed whole for delivery of the ingredients to the stomach and/or lower in the digestive tract.

DETAILED DESCRIPTION OF THE INVENTION

The present invention contains at least 4 different types of components, including, but not limited to, herbal breath cleansing types of ingredients, herbal digestive aid types of ingredients, emulsifiers, a suspending agent that allows the active principles to be suspended in an oil vehicle, and an ingestable oil carrier. These components are contained in a suitable delivery vehicle so that the active agents may be delivered to the stomach or lower in the digestive tract, without significant release in the oral cavity, throat, or esophagus.

Typical breath cleansing ingredients for use in the present invention include, but to, parsley seed, parsley seed oil, ground parsley leaf, bea propolis, and chlorophyll, among others. Preferably, the breath freshening ingredient is parsley seed oil.

Typical digestive aid ingredients for use in the present invention include, but are not limited to, ginger, ginger root extract, licorice, licorice powder, licorice root extract, chamomile, and chamomile extract, among. Preferably, the formulation contains at least three different digestive aid ingredients. Highly preferred digestive aid ingredients are a ginger ingredient (ginger or ginger root extract), a licorice ingredient (licorice powder, or licorice root extract), and a chamomile ingredient (chamomile or chamomile extract). Most preferably, the formulation of the invention has, as the digestive aid ingredients, all three of ginger root extract, licorice root extract, and chamomile extract.

The invention product also has an emulsifier which is selected from the group consisting of natural emulsifiers, synthetic surface active agents, and solid particles emulsifiers, most preferably the natural emulsifiers. The natural emulsifiers are preferably selected from acacia, gelatin, lecithin, and cholesterol, most preferably lecithin. The synthetic surface active agents for use in the present invention may be any of the anionic, cationic, or nonionic types. The anionic surfactants may be alkali metal, ammonium, or mono-, di-, or tri- $C_{2-4}$alkylamine salts of $C_{12-20}$ fatty acids. When used, the alkylamine group of the alkylamine salt is preferably a trialkylamine salt in which each of the alkyl groups of the trialkylamine may be the same or different, but preferably they are all the same. The alkyl group of the alkylamine is preferably ethyl. The anionic surfactants of the invention may also be alkali metal salts of fatty alcohol sulfate esters or alkyl polyoxyethylene sulfates or sulfonates such as dioctyl sodium sulfosuccinate. In each of the above, the alkali metal is preferably sodium or potassium. Cationic surfactants for use in the present invention are typically the quaternary ammonium surfactants, preferably cetyltrimethylammonium halide or lauryldimethylbenzylammonium halide, where the halide is preferably chloride or bromide. The nonionic surfactants for use in the invention include polyoxyethylene $C_{12-20}$fatty alcohol ethers, sorbitan $C_{12-20}$fatty acid esters, and polyoxyethylene sorbitan $C_{12-20}$fatty acid esters. Solid particle emulsifiers for the present invention include bentonite and veegum.

Exemplary useful synthetic surfactants within the above include, without limitation, sorbitan trioleate, propylene glycerol monostearate, glyceryl monostearate, propylene glycol monolaurate, sorbitan monostearate, glyceryl monostearate, sorbitan monolaurate, polyoxyethylene-4-lauryl ether, polyethylene glycol 400 monostearate, polyoxyethylene-4-sorbitan monolaurate, polyoxyethylene-20-sorbitan monopalmitate, polyoxyethylene-40-stearate, sodium oleate, and sodium lauryl sulfate.

In addition to the primary emulsifiers (which may be used in combination), an auxiliary emulsifier selected from cetyl alcohol, glyceryl monostearate, methylcellulose, carboxymethylcellulose, sodium carboxymethylcellulose and stearic acid may be employed as needed for a particular formulation. Also, in place of or inaddition to, one may employ typical pharmaceutically acceptable or food quality viscosity enhancers or thickeners. Those of ordinary skill will be able to select the appropriate ones from the many available such as ethylcellulose, propylcellulose, etc, starch, polyethylene glycols, and other polymeric thickeners known in the pharmaceutical and food arts.

The last of the required components is the suspending agent (hereinafter referred to as the waxy suspending agent) for suspending the other components in the ingestable oil vehicle. This may be of virtually any type which permits the suspension of the other ingredients in the oil vehicle. Preferably, it is selected from a one or more ingestable waxes known in the pharmaceutical and food arts, more preferably a beeswax, most preferably yellow beeswax.

In the present invention, the breath freshening component is generally present in an amount of from about 3.4 to about 12.5 weight % of the required ingredients, preferably of the entire formulation. More preferably, the breath freshening component is about 6 to about 7 weight % of the required ingredients, more preferably of the entire formulation. In the preferred embodiment comprising parsley seed oil and sunflower seed oil, the sunflower seed oil:parsley seed oil is about 32.5:1 to about 32.5:9, preferably about 32.5:2 to about 32.5:5, most preferably 32.5:3.

The digestive aid components, based on extracts (generally a 3:1 or 4:1 extract relative to the powdered herb) comprise about 5 to about 29 weight %, preferably about 8 to about 16.2 weight %, more preferably about 10 weight % of the required ingredients, preferably of the entire formulation. In the preferred embodiment where at least three digestive aid agents are present they are generally present within the ratios of about 2-40:2–40:2-40, preferably about 3-8:3–8:3–8, most preferably about 3-6:3–6:3-6. In the especially preferred embodiment having ginger root extract, licorice root extract, and chamomile extract as the required digestive aids, the ginger extract:licorice extract:chamomile extract ratio is about 2-6:2–8:4-10, more preferably about 3:4:6.

The emulsifier comprises about 1–8 weight %, preferably about 2–6 weight %, more preferably about 3.5–4.3 weight % and most preferably about 3.75 to about 3.9 weight % of the required components, most preferably of the entire formulation.

The waxy suspending agent is present in an amount of about 5 weight % to about 19 weight %, preferably about 9 weight % to about 11 weight %, more preferably about 10.8 weight % to about 11.2 weight %, most preferably about 10.4 weight % of the required ingredient, most preferably of the entire formulation.

The ingestable oil vehicle is preferably selected from safflower oil, sunflower oil, soybean oil, canola oil, peanut oil, corn oil olive oil, etc., most preferably sunflower oil. It comprises about 47 to about 78 weight %, preferably about 63 to about 70 weight % more preferably about 60 to about 68 weight %, most preferably about 63 to about 65 weight % weight % of the required ingredients, most preferably of the entire formulation.

In the preferred embodiments having ginger extract, licorice extract, and chamomile extract as the digestive aids, parsley seed oil as the breath freshener, lecithin as the emulsifier and a beeswax as the waxy suspending agent, and sunflower oil as the ingestible oil vehicle, these ingredients are present in amounts (based on the required ingredients, but preferably based on the entire formulation):

ginger root extract from about 1.7 to about 6.8 weight %, preferably about 3 to 4 weight %; licorice root extract from about 2.4 to about 8.9 weight % preferably about 4 to 5 weight %; chamomile extract from about 3.5 to about 13 weight %, preferably about 6.7 to 7.2 weight %; parsley seed oil from about 3.4 to about 12.5 weight %, preferably about 6.5 to 7.0 weight %; sunflower seed oil from about 47 to about 78 weight %, preferably about 55 to 70 weight %; lecithin from about 2, to about 6 weight %, preferably about 3.5 to about 4.3 weight %; and beeswax from about 5 to about 19 weight %, preferably about 9 to about 11 weight%.

The dosing of the capsules as provided by the present invention is such as to deliver, in one to four capsules, which may be given as a single dose or in divided doses, a total sunflower seed oil amount of between about 57 and about 175 mg, preferably about 85 to about 145 mg, most preferably about 115 mg. Based on the preferred formulation containing 115.2 mg of sunflower seed oil, the typical dose of the invention formulation is 1–2 dosage units after any meal or snack in which offensive breath odor control and/or digestion aid is deemed necessary.

The product of the invention is prepared by warming and mixing (in either order) the ingestable oily vehicle and the waxy suspending agent so that the waxy suspending agent melts and blends with the vehicle. This is generally accomplished in the range of 65° C. to about 70° C. Once this is accomplished, the digestive aid components may be added along with the emulsifier, in any order or all together. The mixture is then cooled to a temperature between about 35° C. and about 45° C., at which point the breath freshener ingredients are added. The resulting mixture is then ready to be put up into an appropriate dosage form, which may be soft or hard gelatin capsules or tablets as desired. Alternatively, once the waxy suspending agent is melted together with the ingestable oily vehicle, the mixture may be cooled at any time thereafter. As long as the mixture temperature is below about 45° C., the breath freshener component may be added, regardless of the order of addition of any of the other ingredients.

The invention will be more clearly understood from the following examples which are intended only to exemplify, but not limit the invention.

EXAMPLES

Example 1

555 capsules are prepared having the following formulation and an encapsulated weight of about 180 mg each:

| Ingredient | Weight in grams |
|---|---|
| Ginger Root Extract | 1.700 |
| Licorice Root Extract | 2.400 |
| Chamomile Extract | 3.500 |
| Parsley Seed Oil | 6.667 |
| Sunflower Seed Oil | 71.455 |
| Lecithin | 3.878 |
| Beeswax | 10.400 |
| | 100.000 |

The beeswax is added to the sunflower seed oil and the resulting mixture is heated to about 65° C. to about 70° C. in order to melt the components together. to this mixture the three extracts are added. The lecithin is then blended in and the mixture is allowed to cool to under about 40° C. finally, the parsley seed oil is blended in and the entire mixture is encapsulated in standard (gelatin/glycerin/water) softgel capsules to yield capsules having a fill weight of about 180 mg each.

Example 2

555 capsules are prepared having the following formulation and an encapsulated weight of about 180 mg each:

| Ingredient | Weight in grams |
|---|---|
| Ginger Root Extract | 6.472 |
| Licorice Root Extract | 8.630 |
| Chamomile Extract | 12.944 |
| Parsley Seed Oil | 5.667 |
| Sunflower Seed Oil | 57.222 |
| Lecithin | 3.878 |
| Beeswax | 5.186 |
| | 100.000 |

The capsules are prepared in the same manner as in Example 1.

Example 3

555 capsules are prepared having the following formulation and an encapsulated weight of about 180 mg each:

| Ingredient | Weight in grams |
|---|---|
| Ginger Root Extract | 3.472 |
| Licorice Root Extract | 4.630 |
| Chamomile Extract | 6.944 |
| Parsley Seed Oil | 6.667 |
| Sunflower Seed Oil | 64.009 |
| Lecithin | 3.878 |
| Beeswax | 10.400 |
| | 100.000 |

The capsules are prepared in the same manner as in Example 1.

Example 4

In a similar manner to Examples 1–3, capsules of the invention can be prepared using the components listed below in the amounts shown:

| | Weight in grams | | | |
|---|---|---|---|---|
| Ingredient | Variant A | Variant B | Variant C | Variant D |
| Digestive Aid | | | | |
| Ginger Root Extract | 4.472 | 2.472 | 2.802 | 3.472 |
| Licorice Root Extract | 4.130 | 5.130 | — | 6.630 |
| Chamomile Extract | 6.444 | 7.444 | 9.244 | 8.416 |
| Breath Freshener | | | | |
| Parsley Seed Oil | 6.667 | 6.667 | 6.667 | 6.667 |
| Emulsifier | | | | |
| Lecithin | 3.878 | 3.878 | 3.878 | 3.878 |
| Suspending Agent | | | | |
| Beeswax | 10.400 | 10.400 | 10.400 | 10.400 |
| Ingestable oily vehicle | | | | |
| Sunflower Seed Oil | 60.537 | 60.537 | 60.537 | 60.537 |
| | 100.000 | 100.000 | 100.000 | 100.000 |

Example 5

In a similar manner to Examples 1–3, capsules of the invention can be prepared using the components listed below in the amounts shown:

| Ingredient | Variant E | Variant F | Variant G | Variant H |
|---|---|---|---|---|
| Digestive Aid | | | | |
| Ginger Root Extract | 3.472 | 3.472 | 3.472 | 3.472 |
| Licorice Root Extract | 4.630 | 4.630 | 4.630 | 4.630 |
| Chamomile Extract | 6.944 | 6.944 | 6.944 | 6.944 |
| Breath Freshener | | | | |
| Parsley Seed Oil | — | 6.667 | 6.667 | 6.667 |
| Chlorophyll | 6.667 | — | — | — |
| Bea Propolis | — | 6.667 | — | — |
| Emulsifier | | | | |
| Lecithin | 3.878 | 2.878 | — | — |
| Acacia | — | — | 3.878 | — |
| Cholesterol | — | — | — | 3.878 |
| PEG 400 monostearate | — | 1.000 | — | — |
| Suspending Agent | | | | |
| Beeswax | 10.400 | 10.400 | 10.400 | 10.400 |
| Ingestable oily vehicle | | | | |
| Sunflower Seed Oil | 64.009 | 57.342 | 64.009 | 64.009 |
| | 100.000 | 100.000 | 100.000 | 100.000 |

I/We claim:

1. A breath freshener product in oral ingestion dosage form comprising:

a gelatin capsule; and a semiliquid or liquid breath freshener formulation, contained as a fill formulation in the capsule, the formulation consisting essentially of (a) a breath freshener component;
   (b) an herbal or herbal extract digestive aid component;
   (c) an emulsifier;
   (d) a waxy suspending agent; and
   (e) an ingestable oily vehicle, wherein breath freshener (a) and digestive aid (b) are not the same, the formulation being dissolved or suspended in components (a)–(e) within the capsule.

2. The breath freshener product of claim 1 wherein component (a) is selected from the group consisting of parsley seed oil, parsley leaf, chlorophyll, and bea propolis; component (b) is selected from the group consisting of ginger root extract, licorice root extract, and chamomile extract; component (c) is selected from the group consisting of natural emulsifiers, synthetic emulsifiers, and solid particle emulsifiers; component (d) is an ingestible wax; and component (e) is selected from the group consisting of safflower oil, sunflower oil, soybean oil, canola oil, peanut oil, corn oil and olive oil.

3. The product of claim 1 wherein the product is a softgel capsule.

4. The product of claim 3 wherein the capsule consists essentially of gelatin, glycerin and water.

5. A method of freshening breath in a mammal in need of such treatment, comprising the step of administering to the mammal the breath freshener product of claim 1, wherein the breath freshener product is swallowed whole by the mammal.

6. The method of claim 5 wherein the mammal is a domesticated pet or a human.

7. The method of claim 5 wherein the mammal is a human.

8. The method of claim 5 wherein the mammal is a farm animal.

* * * * *